(12) United States Patent
Luo et al.

(10) Patent No.: US 10,312,759 B2
(45) Date of Patent: Jun. 4, 2019

(54) MOTOR WITH ELASTIC ELEMENT DEFORMABLE IN DIFFERENT DIRECTIONS

(71) Applicant: NINGBO SEAGO ELECTRIC CO., LTD, Ningbo (CN)

(72) Inventors: Ning Luo, Ningbo (CN); Yanzhong Cai, Leping (CN); Liangliang Cao, Jiujiang (CN); Yuxiang Li, Fuyang (CN)

(73) Assignee: NINGBO SEAGO ELECTRIC CO., LTD., Ningbo (CN)

( * ) Notice: Subject to any disclaimer, the term of this patent is extended or adjusted under 35 U.S.C. 154(b) by 251 days.

(21) Appl. No.: 15/374,368

(22) Filed: Dec. 9, 2016

(65) Prior Publication Data

US 2017/0271935 A1    Sep. 21, 2017

(30) Foreign Application Priority Data

Mar. 16, 2016   (CN) .......................... 2016 1 0150002

(51) Int. Cl.
| | |
|---|---|
| H02K 1/34 | (2006.01) |
| H02K 33/02 | (2006.01) |
| H02K 1/14 | (2006.01) |
| H02K 1/27 | (2006.01) |
| A61C 17/34 | (2006.01) |
| H02K 7/00 | (2006.01) |

(52) U.S. Cl.
CPC ........... *H02K 1/34* (2013.01); *A61C 17/3481* (2013.01); *H02K 1/143* (2013.01); *H02K 1/2726* (2013.01); *H02K 7/003* (2013.01); *H02K 33/02* (2013.01)

(58) Field of Classification Search
CPC ........ H02K 1/34; H02K 1/143; H02K 1/2726; H02K 7/003; H02K 33/02; A61C 17/3481
See application file for complete search history.

(56) References Cited

U.S. PATENT DOCUMENTS

| | | | | |
|---|---|---|---|---|
| 4,220,878 A | * | 9/1980 | Asano ..................... | H01F 7/066 310/13 |
| 5,727,273 A | * | 3/1998 | Pai ......................... | A61C 17/16 15/22.1 |

(Continued)

*Primary Examiner* — Emily P Pham
(74) *Attorney, Agent, or Firm* — Schmeiser, Olsen & Watts LLP

(57) ABSTRACT

A motor comprises an enclosure, a stator and a rotor, the stator comprising a first electromagnetic group and a second electromagnetic group between which the rotor is inserted, the rotor comprising a rotating shaft and a magnetic part installed around the outer wall of the rotating shaft, the motor further comprising an elastic element with a first contact part fixed on rear cover of the enclosure and a second contact part connected with the rotating shaft, wherein the elastic element is elastically deformable in at least two different directions. The motor is applicable to electric toothbrushes, shavers, loudspeakers, electric hammers, stirrers, refrigerators, sewing machines, packaging and bundling machines, electromagnetic pumps, etc. A rotating shaft of the electric toothbrush using the motor has the effects of high-frequency shimming and high-frequency knocking vibration, and the dental calculi on the dental surface are crushed via high-frequency knock, with higher cleaning effect.

12 Claims, 12 Drawing Sheets

(56) References Cited

U.S. PATENT DOCUMENTS

| | | | |
|---|---|---|---|
| 2005/0235438 A1* | 10/2005 | Motohashi | A61C 17/3472 15/22.1 |
| 2007/0040457 A1* | 2/2007 | Shimizu | A61C 17/3445 310/15 |
| 2009/0243405 A1* | 10/2009 | Luo | A61C 17/3418 310/38 |
| 2010/0253160 A1* | 10/2010 | Jones | H02K 1/185 310/43 |
| 2011/0214239 A1* | 9/2011 | Kagami | A61C 17/32 15/22.1 |
| 2013/0207575 A1* | 8/2013 | Bax | A61C 17/3418 318/128 |
| 2016/0218576 A1* | 7/2016 | Luo | H02K 33/16 |

* cited by examiner

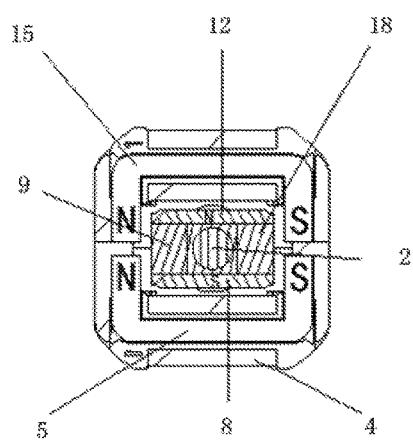
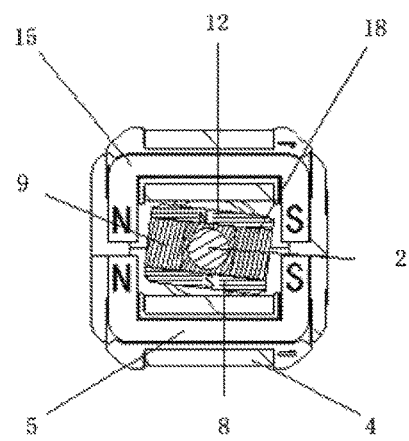
Fig. 5a
Fig. 5b

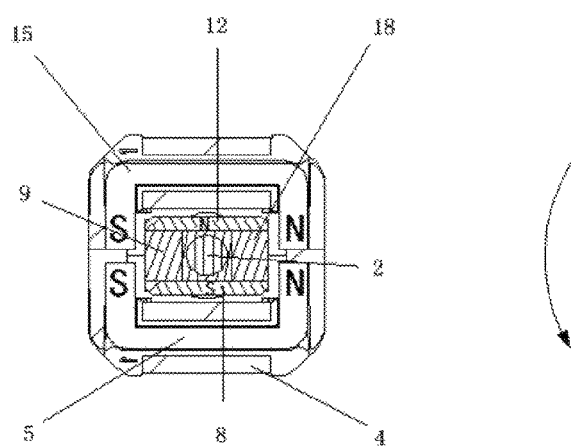 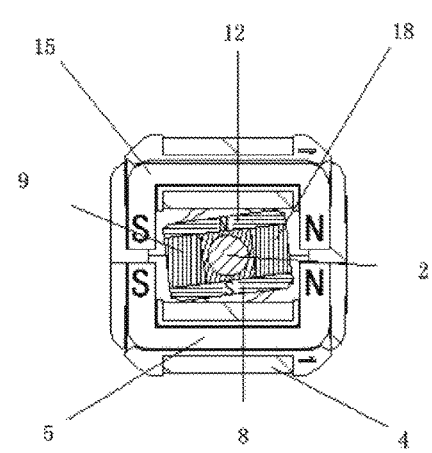
Fig. 5c                                   Fig. 5d

MOTOR WITH ELASTIC ELEMENT DEFORMABLE IN DIFFERENT DIRECTIONS

FIELD OF THE INVENTION

The present invention relates to the field of electric motors, and particularly relates to a motor.

BACKGROUND OF THE INVENTION

With continuous development of the society, people attach increasingly greater importance to oral health, and also pay more and more attention to daily maintenance of teeth. Dental calculi, as an important pathogenic factor of periodontal diseases, refers to dental plaque and debris which are mineralized or being mineralized on the dental face, and are composed of 75% of calcium phosphate, 15-25% of water, organic matters, manganese phosphate, mineral acid calcium as well as trace potassium, sodium and iron. It is difficult to clear the dental calculi with a common toothbrush, and the dental calculi are easily and quickly deposited on the surface of teeth again even if being thoroughly scaled in a stomatological hospital.

At present, many electric toothbrushes appear in the market, e.g., rotating electric toothbrushes, sonic vibrating electric toothbrushes and sonic swinging electric toothbrushes. Because the motors of the electric toothbrushes in the market can only drive the toothbrushes to swing left and right, so that the toothbrushes periodically rub the surfaces of teeth left and right, thus only the superficial layers of dental calculi can be removed, and the dental calculi cannot be cleared deeply.

SUMMARY OF THE INVENTION

Technical Problem

In view of this, the technical problem to be solved by the present invention is to provide a motor of which a rotor can move in multiple directions.

Solution

In order to solve the above technical problem, an embodiment of the present invention provides a motor, including an enclosure, a stator and a rotor, the stator including a first electromagnetic group and a second electromagnetic group, the rotor being inserted between the first electromagnetic group and the second electromagnetic group, wherein the rotor includes a rotating shaft and a magnetic part installed around the outer wall of the rotating shaft, the motor further including:

an elastic element, with a first contact part fixed on a rear cover of the enclosure, and a second contact part connected with the rotating shaft, wherein the elastic element is elastically deformable in at least two different directions.

For the above motor, in one possible implementation, the first contact part of the elastic element is installed in a groove of the rear cover.

For the above motor, in one possible implementation, the tail end of the rotating shaft is provided with at least one clamping groove, and the second contact part of the elastic element is fixed at the tail end of the rotating shaft via the clamping groove.

For the above motor, in one possible implementation, the elastic element is an S-shaped spring.

For the above motor, in one possible implementation, the rear cover and the S-shaped spring are injection molded integrally.

For the above motor, in one possible implementation, the rotor further includes a rotating shaft injection-molded part, which is used for integrally injection molding of the rotating shaft and the magnetic part installed around the outer wall of the rotating shaft.

For the above motor, in one possible implementation, the magnetic part includes a first magnet, a second magnet, a first magnetic conductive plate and a second magnetic conductive plate;

wherein the first magnet and the second magnet are respectively embedded into two opposite sides of the rotating shaft injection-molded part, and the first magnetic conductive plate and the second magnetic conductive plate are respectively fixed on the other two opposite sides of the rotating shaft injection-molded part and respectively in contact with the first magnet and the second magnet.

For the above motor, in one possible implementation, the first electromagnetic group and the second electromagnetic group are symmetrically fixed to form a cavity, and the magnetic part of the rotor is inserted into the cavity;

wherein the first electromagnetic group includes a first magnetized part and a first coil wound on the first magnetized part, and the second electromagnetic group includes a second magnetized part and a second coil wound on the second magnetized part.

For the above motor, in one possible implementation, the enclosure further includes a first body shell, a second body shell and a front cover;

the first body shell and the second body shell enclose the magnetic part from outside, the front cover is sleeved on the rotating shaft and connected with the front ends of the first body shell and the second body shell, and the rear cover is connected with the rear ends of the first body shell and the second body shell;

the first body shell and the second body shell are respectively provided with a first installation groove, a second installation groove and electromagnetic group fixing parts, and through the electromagnetic group fixing parts, the first electromagnetic group is installed in the first installation groove and the second electromagnetic group is installed in the second installation groove.

For the above motor, in one possible implementation, the rotating shaft is sleeved with a bearing, and the bearing is installed in a bearing groove of the front cover.

For the above motor, in one possible implementation, clearances are formed between the tails of the first body shell and the second body shell and the rotating shaft.

For the above motor, in one possible implementation, an elastic body is arranged in front of the clearances.

Beneficial Effects

The motor of the present invention is provided with an elastic element having elastic deformation in multiple directions, so that the rotating shaft of the motor can move in multiple directions, e.g., rotating left and right and vibrating up and down. The motor can be applied to an electric toothbrush, a shaver, a loudspeaker, an electric hammer, a stirrer, a refrigerator, a sewing machine, a packaging and bundling machine, an electromagnetic pump, etc. Taking the electric toothbrush using the motor with the above structure as an example, the rotating shaft of the toothbrush has the effects of high-frequency shimmy and high-frequency knocking vibration at the same time, and the dental calculi on the dental surface can be crushed via high-frequency knock, so that a higher cleaning effect is achieved.

Other features and aspects of the present invention will be apparent from the following detailed description of the exemplary embodiments with reference to the accompanying drawings.

BRIEF DESCRIPTION OF THE DRAWINGS

The accompanying drawings included in the specification and constituting a part of the specification, together with the specification, illustrate the exemplary embodiments, features and aspects of the present invention and are used for interpreting the principle of the present invention.

FIGS. 5a-5d show schematic diagrams of the rotating principle of the rotor according to another embodiment of the present invention;

LIST OF REFERENCE SIGNS

Figure 1A:
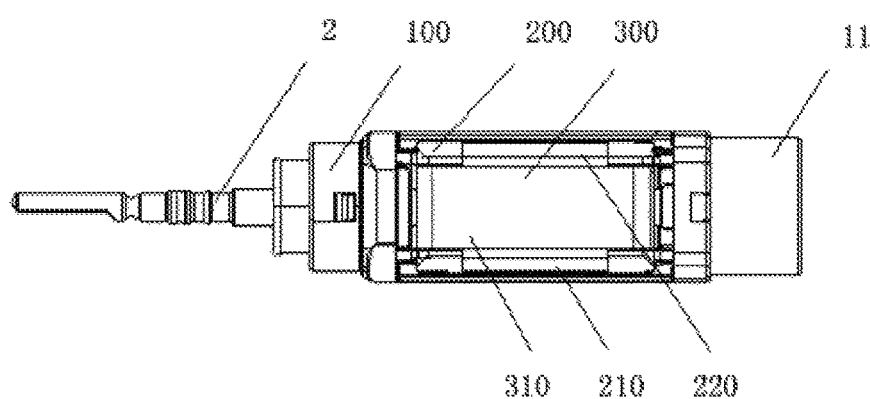
FIG. 1a shows a schematic structural diagram of a motor according to an embodiment of the present invention.

100: enclosure; 200: stator; 300: rotor;
210: first electromagnetic group; 220: second electromagnetic group; 310: magnetic part;
1: front cover; 2: rotating shaft; 3: first electromagnetic group fixing part;
4: first coil; 5: first magnetized part; 6: second electromagnetic group fixing part;
7: first body shell; 8: first magnetic conductive plate; 9: first magnet;
10: S-shaped spring; 10A: first end; 10B: second end;
10C: middle rod; 11: rear cover; 12: second magnetic conductive plate;
13: third electromagnetic group fixing part; 14: second coil; 15: second magnetized part;
16: fourth electromagnetic group fixing part; 17: second body shell; 18: second magnet;
19: bearing; 20: elastic body; 21: rotating shaft injection-molded part.

DETAILED DESCRIPTION OF THE EMBODIMENTS

Various exemplary embodiments, features and aspects of the present invention will be described in detail below with reference to the accompanying drawings. The same signs in the drawings represent elements with the same or similar functions. Although various aspects of the embodiments are shown in the drawings, the drawings do not need to be drawn to scale unless otherwise indicated.

The special word "exemplary" herein means "using as an example or an embodiment or illustrative". Any "exemplary" embodiment described herein should not be interpreted as being superior to or better than other embodiments.

In addition, numerous specific details are given in the specific embodiments below in order to better illustrate the present invention. Those skilled in the art should understand that the present invention can also be implemented without some specific details. In some embodiments, the methods, means, elements and circuits known to those skilled in the art are not described in detail, thereby highlighting the theme of the present invention.

Embodiment 1

FIG. 1a shows a schematic structural diagram of a motor according to an embodiment of the present invention. As shown in FIG. 1a, the motor mainly includes an enclosure 100, a stator 200 and a rotor 300. Specifically, the stator 200 includes a first electromagnetic group 210 and a second electromagnetic group 220, the rotor 300 is inserted between the first electromagnetic group 210 and the second electromagnetic group 220, and the rotor 300 includes a rotating shaft 2 and a magnetic part 310 installed around the outer wall of the rotating shaft 2. The motor further includes an elastic element (not shown in the figure), with a first contact part fixed on a rear cover 11 of the enclosure 100, and a second contact part connected with the rotating shaft 2, wherein the elastic element is elastically deformable in at least two different directions.

The motor is an electromagnetic device for converting or transferring electric energy according to the law of electromagnetic induction, and is widely applied to electric equipment. The elastic element is the one with resilience, and can generate a restoring force during deformation thereof to restore its original shape. The stator 200 of the motor of this embodiment adopts two electromagnetic groups, and the magnetic part 310 of the rotor 300 is preferably a permanent magnet, so that the rotor 300 is lighter in weight and quick in dynamic response and has a larger output torque in the case of providing an equal ampere-turn current. Meanwhile, by adopting the above structure, the motor is more convenient to install and detach, and later maintenance cost can be reduced.

Figure 1B:
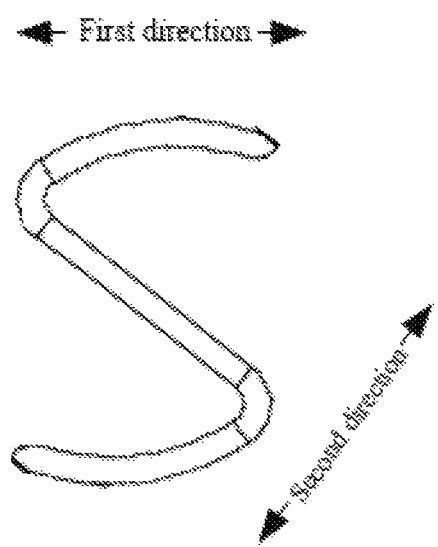
FIG. 1b shows a schematic diagram of deformation directions of an elastic element of the motor according to an embodiment of the present invention.
Figure 2A:
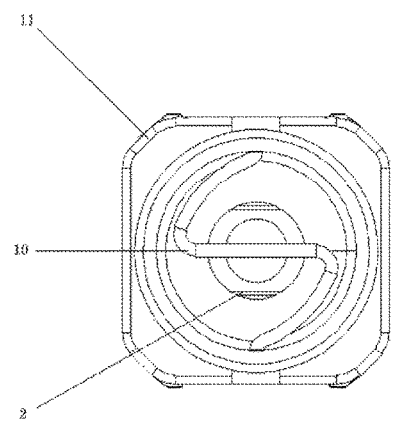
FIGS. 2a-2d show schematic diagrams of the reset principle of an S-shaped spring according to another embodiment of the present invention.
Figure 2B:
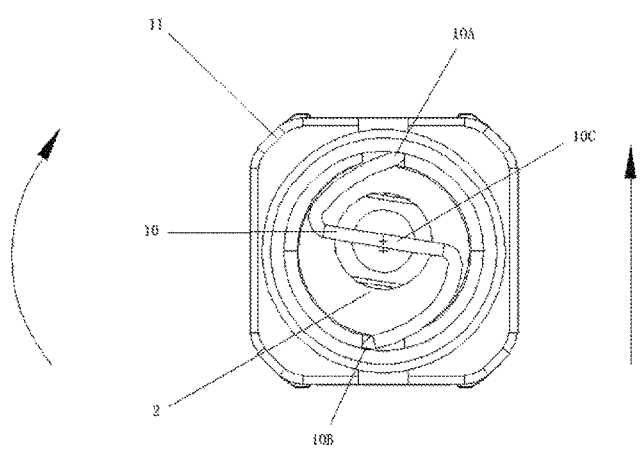
Figure 2C:
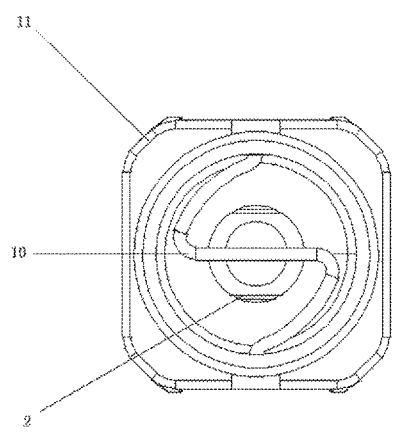
Figure 2D:
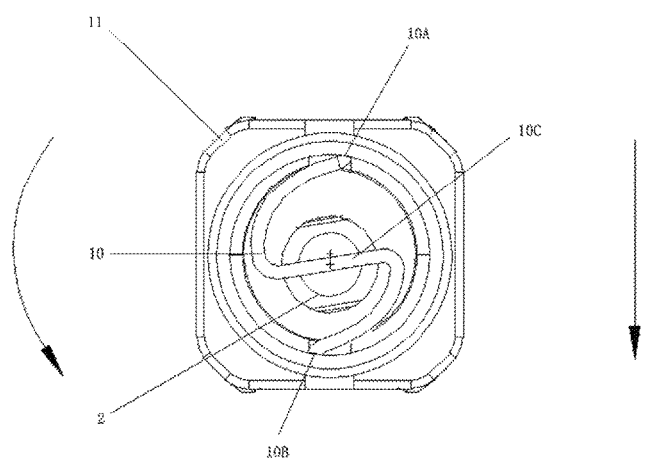

In one possible implementation, the first contact part of the elastic element is installed in a groove of the rear cover 11. The tail end of the rotating shaft 2 is provided with at least one clamping groove, and the second contact part of the elastic element is fixed at the tail end of the rotating shaft 2 via the clamping groove. The elastic element is preferably an S-shaped spring 10, and as shown in FIG. 1b, the S-shaped spring 10 is elastically deformable in at least two directions. For example, the S-shaped spring 10 can be stretched or extruded in the first direction and the second direction.

Specifically, as shown in FIGS. 2a to 2d, the first contact part of the S-shaped spring 10 includes a first end 10A and a second end 10B, the rear cover 11 of the motor is provided with two symmetrical grooves, the grooves have movable spaces, and the first end 10A and the second end 10B are respectively installed in the corresponding grooves. Preferably, the S-shaped spring 10 and the rear cover 11 have an injection molded integrally structure. The second contact part of the S-shaped spring 10 is a middle rod 10C thereof, the tail of the rotating shaft 2 is provided with a long clamping groove, the middle rod 10C of the S-shaped spring 10 is fixed in the long clamping groove of the rotating shaft 2, and the rotating shaft 2 and the S-shaped spring 10 are detachable. By adopting the detachable structure, the tail cover 11 and the elastic element of the motor can be replaced, thereby prolonging the service life of the motor and reducing the cost.

Further, when the first electromagnetic group 210 and the second electromagnetic group 220 of the stator 200 are powered on to generate a magnetic field, the rotor 300 inserted into the stator 200 rotates under the action of a magnetic thrust, and deviates from the initial axis. Thus, the rotating shaft 2 of the rotor 300 drives the S-shaped spring 10 to arrive at the position shown in FIG. 2b. At the moment, the S-shaped spring 10 is elastically deformed in two different directions as shown in FIG. 1b. In this case, the rotor 300 can return to the initial position under the action of a restoring force in the two directions of the S-shaped spring 10. Then, the direction of the magnetic thrust can be changed by changing the current direction of the stator 200, so that the rotor 300 rotates in the direction opposite to that of the previous phase and deviates from the initial axis. Thus, the rotor 300 drives the S-shaped spring 10 to arrive at the position shown in FIG. 2d. In this case, the rotor 300 returns to the initial position again under the action of the restoring force in the two directions of the S-shaped spring 10. With the process repeated cyclically, the rotor 300 rotates reciprocally with certain amplitude and vibrates in the vertical direction of the rotating shaft 2.

The S-shaped spring 10 has the characteristics that the generated noise is low, the restoration is strong and the spring is easy to install. Specifically, two ends of the S-shaped spring 10 are bent in a non-semicircular arc manner, thereby improving the elastic restoration strength of the two ends. With different radians of the semicircular arc, the resulting flexibility and rigidity are different, and the performance is easy to control. Meanwhile, the S-shaped spring 10 is simple in installation process and good in location dimension, has good coaxial characteristic, and can well ensure the concentric position with the rotating shaft 2.

The S-shaped spring 10 adopted in this embodiment is merely an example, and an elastic element of other type, which is similar to the S-shaped spring 10 capable of elastic deformation in multiple directions, can also be adopted, e.g., an Z-shaped, M-shaped, X-shaped, U-shaped, I-shaped or N-shaped spring, etc.

The motor of this embodiment is applicable to an electric toothbrush, a shaver, a loudspeaker, an electric hammer, a stirrer, a refrigerator, a sewing machine, a packaging and bundling machine, an electromagnetic pump, etc. Taking the electric toothbrush using the motor with the above structure as an example, the rotating shaft of the toothbrush has the effects of high-frequency shimmy and high-frequency knocking vibration at the same time, and the dental calculi on the dental surface can be crushed via high-frequency knock, so that a higher cleaning effect is achieved.

Embodiment 2

Figure 3A:
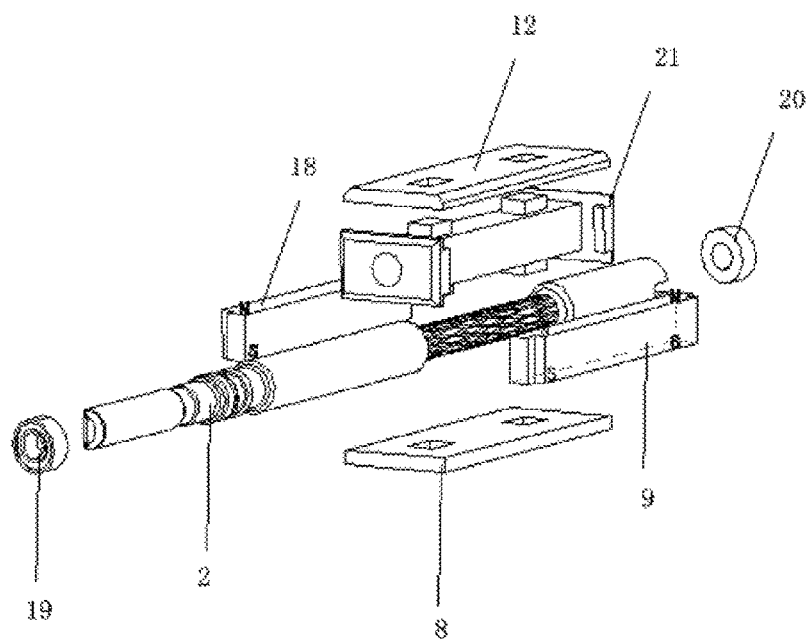
FIGS. 3a-3b show schematic structural diagrams of a rotor of the motor according to another embodiment of the present invention.
Figure 3B:
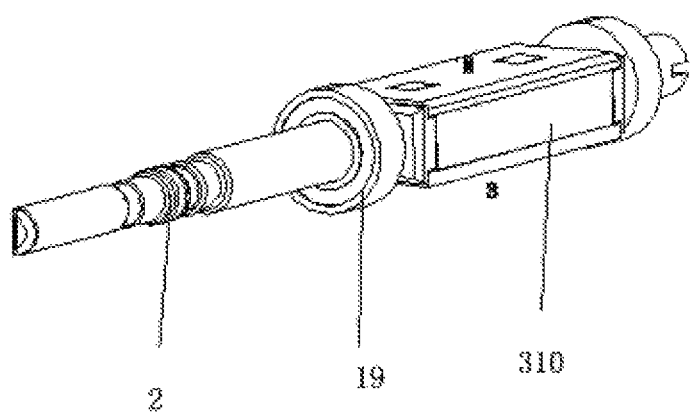

FIGS. 3a-3b show schematic structural diagrams of the rotor 300 of the motor according to another embodiment of the present invention. The components with the same signs in FIGS. 3a to 3b, 1a to 1b and 2a to 2d have the same meanings, and thus are not redundantly described herein.

Different from the above embodiment, the rotor 300 of the motor in this embodiment further includes a rotating shaft injection-molded part 21, which is used for integrally injection molding of the rotating shaft 2 and the magnetic part 310 installed around the outer wall of the rotating shaft 2. The rotating shaft 2 is preferably an integrated rod. By adopting the integrated rod structure, the stress of the rotating shaft 2 is more uniform, and the rotating shaft 2 is unlikely to break and also produces a smoother movement locus.

In one possible implementation, as shown in FIG. 3a, the magnetic part 310 is installed around the outer wall of the rotating shaft 2 via the rotating shaft injection-molded part 21. Specifically, the magnetic part 310 includes a first magnet 9, a second magnet 18, a first magnetic conductive plate 8 and a second magnetic conductive plate 12. The first magnet 9 and the second magnet 18 are respectively embedded into two opposite sides of the rotating shaft injection-molded part 21. The first magnetic conductive plate 8 and the second magnetic conductive plate 12 are respectively fixed on the other two opposite sides of the rotating shaft injection-molded part 21 and respectively in contact with the first magnet 9 and the second magnet 18.

As shown in FIG. 3a, the first magnet 9 and the second magnet 18, which are in parallel and with consistent polarity directions, are respectively embedded into the two opposite sides of the rotating shaft injection-molded part 21. The first magnetic conductive plate 8 and the second magnetic conductive plate 12 are respectively in contact with the first magnet 9 and the second magnet 18 and cover the contact faces. As shown in FIG. 3b, the rotating shaft 2, the first magnet 9, the second magnet 18, the first magnetic conductive plate 8 and the second magnetic conductive plate 12 are fixed relative to each other into a whole, which can effectively keep the axis consistency of the motor. The first magnet 9 and the second magnet 18 are preferably permanent magnets, the first magnetic conductive plate 8 and the second magnetic conductive plate 12 are preferably plate structures made of a magnetic conductive material, each magnetic conductive plate is provided with through holes for installation on the rotating shaft injection-molded part 21, and the through holes can be sleeved on protrusions of the rotating shaft injection-molded part 21. The shapes of the through holes and the protrusions are not limited, and can be square as shown in the figure or other shape. Of course, the two magnetic conductive plates can also be fixed on the rotating shaft injection-molded part 21 in other way such as bonding, riveting or the like, and this embodiment is not limited thereto.

Figure 4A:
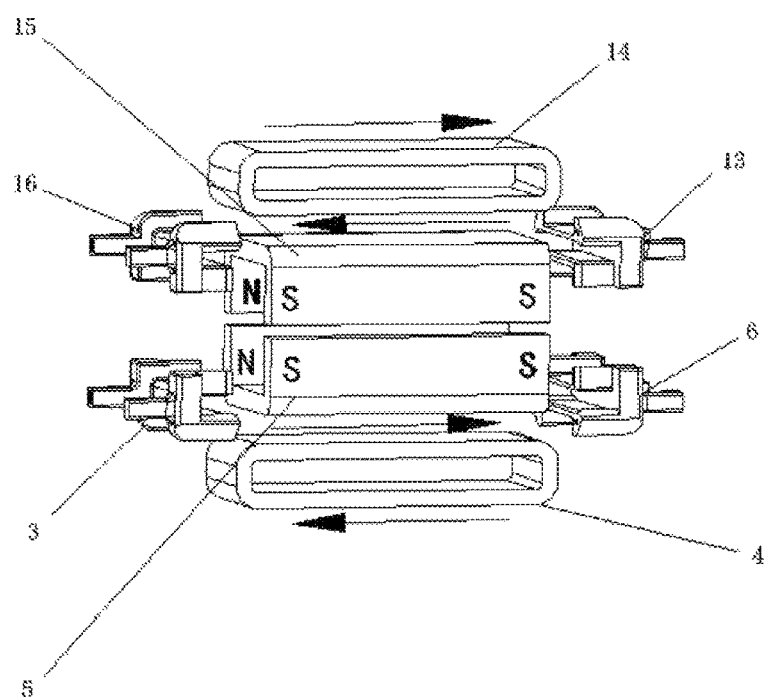
FIGS. 4a-4b show schematic structural diagrams of a stator of the motor according to another embodiment of the present invention.
Figure 4B:
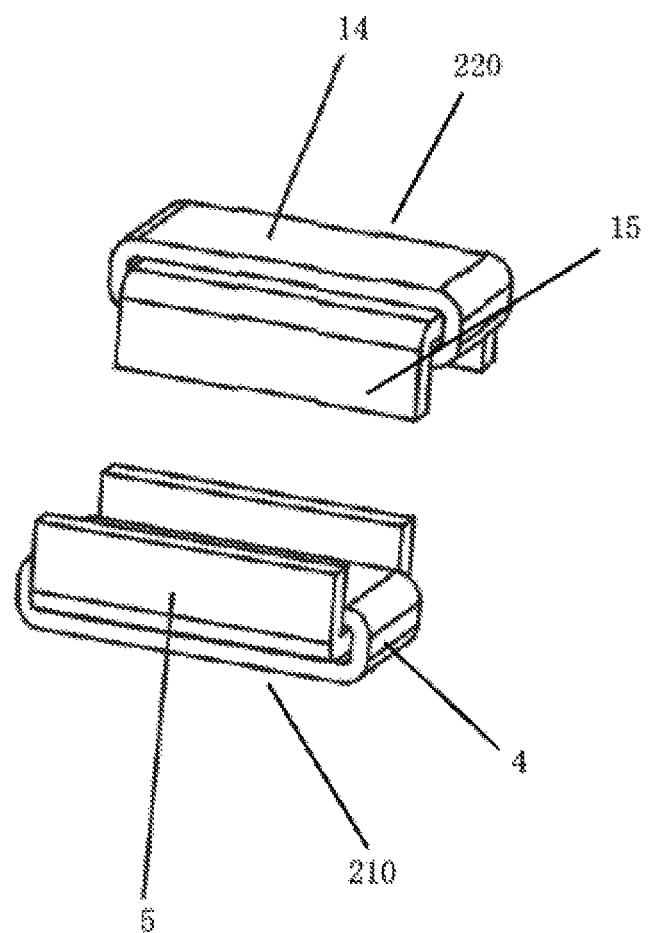

FIGS. 4a-4b show schematic structural diagrams of the stator 200 of the motor according to another embodiment of the present invention. The components with the same signs in FIGS. 4a to 4b, 1a to 1b, 2a to 2d and 3a to 3b have the same meanings, and thus are not redundantly described herein.

Different from the previous embodiment, the stator 200 includes a first electromagnetic group 210 and a second electromagnetic group 220 which are symmetrically fixed to form a cavity, and the magnetic part 310 of the rotor 300 is inserted into the cavity. The first electromagnetic group 210 includes a first magnetized part 5 and a first coil 4 wound on the first magnetized part 5, and the second electromagnetic group includes a second magnetized part 15 and a second coil 14 wound on the second magnetized part 15.

The first magnetized part 5 and the second magnetized part 15 can be made of a magnetized material such as silicon steel or the like. As shown in FIG. 4b, two silicon steel sheets (the first magnetized part 5 and the second magnetized part 15) having U-shaped cross sections and with coils wound thereon respectively are arranged oppositely to form a cavity, and the magnetic part of the rotor 300 is inserted into the cavity. In the working state of the motor, as shown in FIG. 4a, a current in the same direction flows through the first coil 4 and the second coil 14 to generate a magnetic field and magnetize the silicon steel sheets, and the direction of the magnetic field can be judged according to the right-hand rule.

Further, after the first coil 4 and the second coil 14 are powered on, the silicon steel sheets (the first magnetized part 5 and the second magnetized part 15) are magnetized by the electromagnetic field to generate an N-S pole distribution as shown in FIG. 5*a*, and an S-N pole mutually exclusive magnetic field is generated between the silicon steel sheets and the rotor 300. When the direction of the current flowing through the first coil 4 and the second coil 14 is changed, the silicon steel sheets are magnetized by the electromagnetic field to generate an S-N pole distribution as shown in FIG. 5*c*, and an N-S pole mutually exclusive magnetic field between the silicon steel sheets and the rotor 300. The high level and the low level of the power are interchanged according to certain frequency, so that the direction of the magnetic field generated by the stator 200 is opposite, and then the rotating shaft 2 of the motor swings with equal left and right amplitudes under the action of force of the same frequency and different directions, and returns to its normal position under the action of the S-shaped spring 10.

The stator of the motor of this embodiment adopts two electromagnetic groups, and the rotor adopts a permanent magnet structure, so that the rotor is lighter in weight and quick in dynamic response and has a larger output torque in the case of providing an equal ampere-turn current. Meanwhile, by adopting the above structure, the motor is more convenient to install and detach, and later maintenance and repair cost can be reduced.

Embodiment 3

Figure 6:
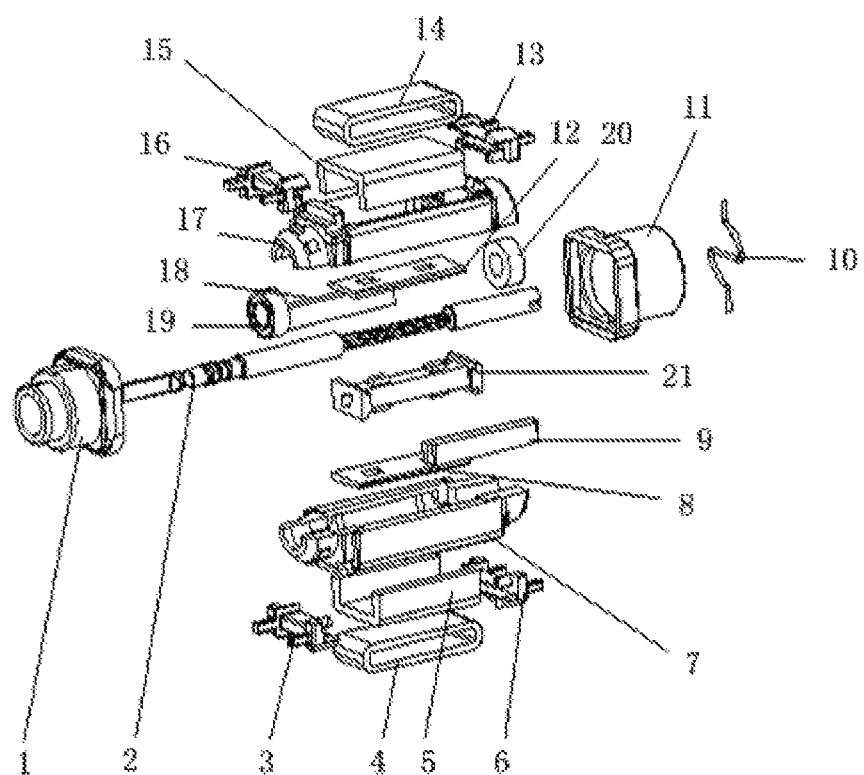
FIG. 6 shows an exploded view of the motor according to another embodiment of the present invention.

FIG. 6 shows an exploded view of the motor according to another embodiment of the present invention. The components with the same signs in FIGS. 6, 1*a* to 1*b*, 2*a* to 2*d*, 3*a* to 3*b*, 4*a* to 4*b* and 5*a* to 5*d* have the same meanings, and thus are not redundantly described herein.

As shown in FIG. 6, the enclosure 100 of the motor can further include a first body shell 7, a second body shell 17 and a front cover 1. The first body shell 7 and the second body shell 17 enclose the magnetic part 310 from outside, the front cover 1 is sleeved on the rotating shaft 2 and connected with the front ends of the first body shell 7 and the second body shell 17, and the rear cover 11 is connected with the rear ends of the first body shell 7 and the second body shell 17. The first body shell 7 and the second body shell 17 are respectively provided with a first installation groove, a second installation groove and electromagnetic group fixing parts 3, 6, 13 and 16, and through the electromagnetic group fixing parts 3, 6, 13 and 16, the first electromagnetic group 210 is installed in the first installation groove and the second electromagnetic group 220 is installed in the second installation groove.

In one possible implementation, the rotating shaft 2 is sleeved with a bearing 19, and the bearing 19 is installed in a bearing groove of the front cover 1.

Specifically, the bearing 19 is sleeved on the rotating shaft 2, a bearing groove is formed in the front cover 1, the bearing 19 is fixed by way of extrusion via the rotating shaft 2 and the front cover 1 in cooperation, and the bearing 19 is mainly used for supporting the rotating shaft 2 of the rotor 300, reducing the friction coefficient thereof during moving and ensuring the rotating precision thereof.

Figure 7:
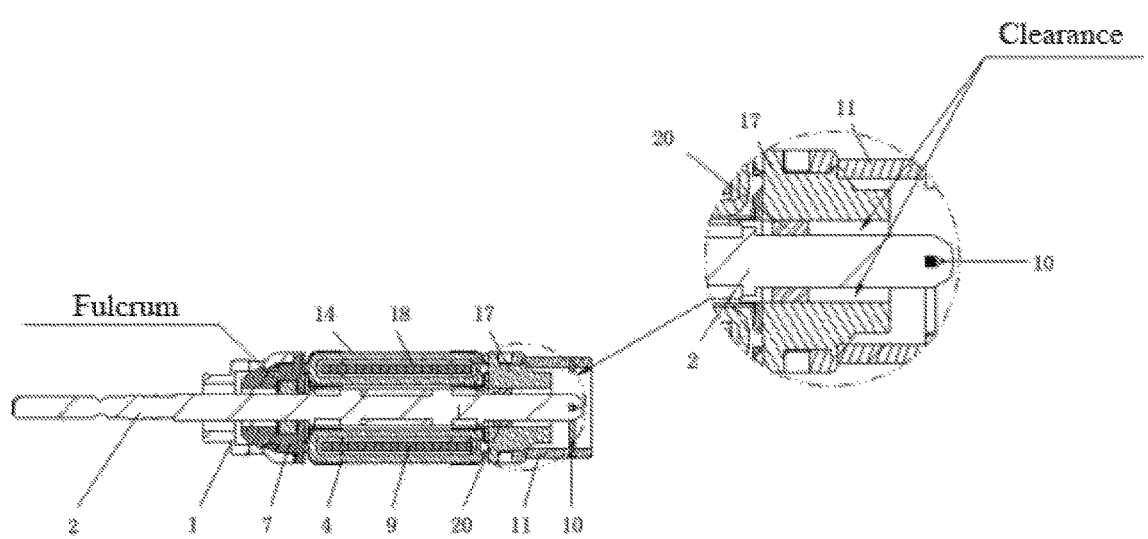
FIG. 7 shows a section view of the motor according to another embodiment of the present invention.

In one possible implementation, clearances are formed between the tail of the first body shell 7 and the rotating shaft 2 and the tail of the second body shell 17 and the rotating shaft 2. Preferably, an elastic body 20 is arranged in front of the clearances. As shown in FIG. 7, clearances are formed between the tails of the first body shell 7 and the second body shell 17 and the rotating shaft 2, so that the obstruction is small when the rotating shaft 2 vibrates in the direction perpendicular to the axis. Meanwhile, an elastic body 20 is arranged at a front end of the clearances, and the elastic body 20 is preferably made of soft rubber and can strengthen the restoration of the swinging motor.

The working principle of the motor of this embodiment is as follows: as shown in FIG. 7, the tail of the rotating shaft 2 is fixed to the S-shaped spring 10, and clearances are formed between the rotating shaft 2 and the tails of the body shells. According to the lever principle, the S-shaped spring 10 and the bearing 19 are used as lever fulcrums, and vibration generated when the rotor 300 swings is utilized, so that the rotor 300 swings left and right and at the same time performs irregular curved vibration using the fulcrum shown in FIG. 7 as an origin. Finally, the rotor 300 returns to the initial position under the actions of flexible restoring force generated by the S-shaped spring 10 and elastic restoration of the elastic body 20, and the process is thus repeated cyclically.

The motor of this embodiment is applicable to an electric toothbrush, a shaver, a loudspeaker, an electric hammer, a stirrer, a refrigerator, a sewing machine, a packaging and bundling machine, an electromagnetic pump, etc. Taking the electric toothbrush using the motor with the above structure as an example, the rotating shaft of the toothbrush has the effect of irregular curved vibration while making high-frequency shimmy, and the dental calculi on the dental surface can be crushed via the irregular curved vibration, so that a higher cleaning effect is achieved.

Described above are merely specific embodiments of the present invention, but the protection scope of the present invention is not limited to this. Any variations or substitutions within the disclosed technical scope of the present invention that are readily conceivable to those skilled in the art shall fall within the protection scope of the present invention. Thus, the protection scope of the present invention shall be defined by the protection scope of the claims.

The invention claimed is:

1. A motor, comprising an enclosure, a stator and a rotor, the stator comprising a first electromagnetic group and a second electromagnetic group, the rotor being inserted between the first electromagnetic group and the second electromagnetic group, wherein the rotor comprises a rotating shaft and a magnetic part installed around an outer wall of the rotating shaft, the motor further comprising:
    an elastic element, with a first contact part fixed on a rear cover of the enclosure, and a second contact part connected with the rotating shaft, wherein the elastic element is elastically deformable in at least two different directions,
    wherein the rotor is configured to, under an action of a restoring force generated by the elastic element, rotate around the rotating shaft and vibrate in a direction vertical to the rotating shaft.

2. The motor of claim 1, wherein the first contact part of the elastic element is installed in a groove of the rear cover.

3. The motor of claim 2, wherein a tail end of the rotating shaft is provided with at least one clamping groove, and the second contact part of the elastic element is fixed at the tail end of the rotating shaft via the clamping groove.

4. The motor of claim 3, wherein the elastic element is an S-shaped spring.

5. The motor of claim 4, wherein the rear cover and the S-shaped spring are injection molded integrally.

6. The motor of claim 1, wherein the rotor further comprises a rotating shaft injection-molded part, which is used for integrally injection molding of the rotating shaft and the magnetic part installed around the outer wall of the rotating shaft.

7. The motor of claim 6, wherein the magnetic part comprises a first magnet, a second magnet, a first magnetic conductive plate and a second magnetic conductive plate;
wherein the first magnet and the second magnet are respectively embedded into two opposite sides of the rotating shaft injection-molded part, and the first magnetic conductive plate and the second magnetic conductive plate are respectively fixed on the other two opposite sides of the rotating shaft injection-molded part and respectively in contact with the first magnet and the second magnet.

8. The motor of claim 1, wherein the first electromagnetic group and the second electromagnetic group are symmetrically fixed to form a cavity, and the magnetic part of the rotor is inserted into the cavity;
wherein the first electromagnetic group comprises a first magnetized part and a first coil wound on the first magnetized part, and the second electromagnetic group comprises a second magnetized part and a second coil wound on the second magnetized part.

9. The motor of claim 1, wherein the enclosure further comprises a first body shell, a second body shell and a front cover;
the first body shell and the second body shell enclose the magnetic part from outside, the front cover is sleeved on the rotating shaft and connected with front ends of the first body shell and the second body shell, and the rear cover is connected with rear ends of the first body shell and the second body shell;
the first body shell and the second body shell are respectively provided with a first installation groove, a second installation groove and electromagnetic group fixing parts, and through the electromagnetic group fixing parts, the first electromagnetic group is installed in the first installation groove and the second electromagnetic group is installed in the second installation groove.

10. The motor of claim 9, wherein the rotating shaft is sleeved with a bearing, and the bearing is installed in a bearing groove of the front cover.

11. The motor of claim 10, wherein clearances are formed between tails of the first body shell and the second body shell and the rotating shaft.

12. The motor of claim 11, wherein an elastic body is arranged in front of the clearances.

* * * * *